US00PP20497P2

(12) United States Plant Patent
Dümmen

(10) Patent No.: US PP20,497 P2
(45) Date of Patent: Nov. 17, 2009

(54) ***VERBENA* PLANT NAMED 'DUEMPSTRAW'**

(50) Latin Name: *Verbena hybrida*
Varietal Denomination: Duempstraw

(75) Inventor: Tobias Dümmen, Rheinberg (DE)

(73) Assignee: Capital Green Investments Ltd., Grand Cayman (KY)

( * ) Notice: Subject to any disclaimer, the term of this patent is extended or adjusted under 35 U.S.C. 154(b) by 405 days.

(21) Appl. No.: 11/807,298

(22) Filed: May 26, 2007

(51) Int. Cl.
*A01H 5/00* (2006.01)

(52) U.S. Cl. ..... Plt./308

(58) Field of Classification Search ..... Plt./308
See application file for complete search history.

*Primary Examiner*—Kent L Bell
(74) *Attorney, Agent, or Firm*—C. A. Whealy

(57) ABSTRACT

A new and distinct cultivar of *Verbena* plant named 'Duempstraw', characterized by its compact, mounding and cascading plant habit; freely branching habit; freely flowering habit; large red-colored flowers that are held above and beyond the foliage in mounded umbels; and resistance to Powdery Mildew.

1 Drawing Sheet

Botanical designation: *Verbena hybrida*
Cultivar denomination: 'DUEMPSTRAW'.

BACKGROUND OF THE INVENTION

The present invention relates to a new and distinct cultivar of *Verbena,* botanically known as *Verbena hybrida*, and hereinafter referred to by the name 'Duempstraw'.

The new *Verbena* is a product of a planned breeding program conducted by the Inventor in Rheinberg, Germany. The objective of the breeding program is to create new uniform *Verbena* cultivars with large and attractive flowers.

The new *Verbena* originated from a cross-pollination made by the Inventor in August, 2002 in Rheinberg, Germany of a proprietary seedling selection of *Verbena hybrida* identified as code number V00-3814-1, not patented, as the female, or seed, parent with a proprietary seedling selection of *Verbena hybrida* identified as code number V00-2813-3, not patented, as the male, or pollen, parent. The new *Verbena* was discovered and selected by the Inventor as a single flowering plant within the progeny of the stated cross-pollination in a controlled environment in Rheinberg, Germany in May, 2005.

Asexual reproduction of the new *Verbena* by terminal cuttings in a controlled environment in Rheinberg, Germany since July, 2005 has shown that the unique features of this new *Verbena* are stable and reproduced true to type in successive generations.

SUMMARY OF THE INVENTION

The cultivar Duempstraw has not been observed under all possible environmental conditions. The phenotype may vary somewhat with variations in environment and cultural practices such as temperature, daylength and light intensity without, however, any variance in genotype.

The following traits have been repeatedly observed and are determined to be the unique characteristics of 'Duempstraw'. These characteristics in combination distinguish 'Duempstraw' as a new and distinct cultivar of *Verbena:*

1. Compact, mounding and cascading plant habit.
2. Freely branching habit.
3. Freely flowering habit.

4. Large red-colored flowers that are held above and beyond the foliage in mounded umbels.
5. Resistant to Powdery Mildew.

Plants of the new *Verbena* can be compared to plants of the female parent selection. Plants of the new *Verbena* differ primarily from plants of the female parent selection in flower color as plants of the female parent selection have purple-colored flowers.

Plants of the new *Verbena* can be compared to plants of the male parent selection. Plants of the new *Verbena* differ from plants of the male parent selection in the following characteristics:

1. Plants of the new *Verbena* have larger leaves than plants of the male parent selection.
2. Plants of the new *Verbena* have larger flowers than plants of the male parent selection.

Plants of the new *Verbena* can be compared to plants of the *Verbena* cultivar Sunmarisu, disclosed in U.S. Plant Pat. No. 11,113. In side-by-side comparisons conducted in Rheinberg, Germany, plants ofthe new *Verbena* differed from plants of the cultivar Sunmarisu in the following characteristics:

1. Plants of the new *Verbena* had longer internodes than plants of the cultivar Sunmarisu.
2. Plants of the new *Verbena* had longer leaves than plants of the cultivar Sunmarisu.
3. Plants of the new *Verbena* had larger flowers than plants of the cultivar Sunmarisu.
4. Plants of the new *Verbena* had longer peduncles than plants of the cultivar Sunmarisu.

BRIEF DESCRIPTION OF THE PHOTOGRAPH

The accompanying colored photograph illustrates the overall appearance of the new *Verbena,* showing the colors as true as it is reasonably possible to obtain in colored reproductions of this type. Colors in the photograph may differ slightly from the color values cited in the detailed botanical description which accurately describe the colors of the new *Verbena.*

The photograph comprises a close-up view of typical leaves and inflorescences of 'Duempstraw'.

DETAILED BOTANICAL DESCRIPTION

The aforementioned photographs and following observations, measurements and values describe plants grown in Rheinberg, Germany in a glass-covered greenhouse during the spring and under conditions which closely approximate commercial production. During the production of the plants, day and night temperatures averaged 18° C. and light levels averaged 4,500 lux. Plants were pinched one time about one week after planting. Plants were about 16 weeks old when the photograph and the description were taken. In the description, color references are made to The Royal Horticultural Society Colour Chart, 1995 Edition, except where general terms of ordinary dictionary significance are used.

Botanical classification: *Verbena hybrida* cultivar Duempstraw.

Parentage:

*Female, or seed, parent.*—Proprietary seedling selection of *Verbena hybrida* identified as code number V00-3814-1, not patented.

*Male, or pollen, parent.*—Proprietary seedling selection of *Verbena hybrida* identified as code number V00-2813-3, not patented.

Propagation:

*Type.*—Terminal cuttings.

*Time to initiate roots.*—About ten days at 20° C.

*Time to produce a rooted cutting, summer.*—About 21 days at 20° C.

*Time to produce a rooted cutting, winter.*—About 25 days at 20° C.

*Root description.*—Fine, fibrous; white in color.

*Rooting habit.*—Freely branching; dense.

Plant description:

*Plant habit.*—Initially upright, then mounding to cascading plant habit; compact growth habit. Freely branching habit with about four to six primary lateral branches with secondary lateral branches potentially forming at every node; pinching enhances lateral branch development; dense and bushy plant habit. Moderately vigorous growth habit.

*Plant height.*—About 15 cm.

*Plant diameter.*—About 20 cm.

Lateral branch description:

*Length.*—About 16 cm.

*Diameter.*—About 2 mm.

*Internode length.*—About 4.75 cm.

*Texture.*—Pubescent.

*Color.*—144A.

Foliage description:

*Arrangement.*—Opposite, simple.

*Length.*—About 4.8 cm.

*Width.*—About 2.5 cm.

*Shape.*—Lanceolate; deeply dissected; doubly pinnatifid.

*Apex.*—Acute.

*Base.*—Attenuate.

*Margin.*—Deeply dissected.

*Texture, upper and lower surfaces.*—Pubescent, coarse.

*Venation pattern.*—Pinnate.

*Color.*—Developing and fully expanded foliage, upper surface: 146A; venation, 146D. Developing and fully expanded foliage, lower surface: 146B; venation, 146D.

*Petiole length.*—About 5 mm.

*Petiole diameter.*—About 2 mm.

*Petiole texture, upper and lower surfaces.*—Smooth, pubescent.

*Petiole color, upper surface.*—146A.

*Petiole color, lower surface.*—146B.

Flower description:

*Flower arrangement and habit.*—Salverform flowers arranged in hemispherical terminal umbels; umbels dense and mounding; numerous umbels covering the entire plant. Flowers face upward or outward. Freely flowering habit with about 50 flowers and flower buds per inflorescence. Flowers not fragrant.

*Natural flowering season.*—Plants flower continuously from the spring through the fall in Germany.

*Flower longevity.*—Individual flowers last about one week on the plant. Flowers persistent.

*Inflorescence size.*—Diameter: About 4.5 cm. Height: About 5.5 cm.

Flowers.—Appearance: Flared trumpet, corolla fused, five-parted. Diameter: About 2.5 cm. Depth: About 2.7 cm.

*Flower buds.*—Length: About 1.6 cm. Diameter: About 3.5 mm. Shape: Oval, tubular. Color: 146A.

Corolla.—Arrangement: Single whorl of five fused petals. Petal lobe length: About 3.3 cm. Petal lobe width: About 1 cm. Petal lobe shape: Obovate. Petal lobe apex: Emarginate to cordate. Petal margin: Entire. Petal texture, upper and lower surfaces: Smooth, glabrous; velvety. Color: Petal, when opening, upper surface: 45B to 45C. Petal, when opening, lower surface: 46C. Petal, fully opened, upper surface: 45B to 45D; color becoming closer to 45C to 45D with development. Petal, fully opened, lower surface: 46D.

Calyx.—Arrangement: Star-shaped calyx with five fused sepals. Sepal length: About 1.3 cm. Sepal width: About 1 mm. Sepal shape: Ligulate. Sepal apex: Acute. Sepal margin: Entire. Sepal texture, upper and lower surfaces: Pubescent, coarse. Sepal color, upper and lower surfaces: 146D and 144A.

Peduncles.—Length: About 7.4 cm. Diameter: About 2 mm. Strength: Strong. Texture: Pubescent. Color: 144A.

Pedicels.—Length: About 0.5 mm. Diameter: About 0.5 mm. Strength: Strong. Texture: Smooth, glabrous. Color: 144A.

Reproductive organs: Stamens: Quantity/arrangement: About four to five per flower, adnate to corolla tube. Filament length: About 1 mm. Filament color: Close to 145D. Anther shape: Oval. Anther length: About 0.75 mm. Anther color: 144B. Pollen amount: Moderate. Pollen color: 2D. Pistils: Quantity: One per flower. Pistil length: About 1.8 cm. Stigma shape: Bi-parted. Stigma color: 144A. Style length: About 1.6 cm. Style color: 144D. Ovary color: 144C. Fruits/seed: Fruit and seed development have not been observed.

Temperature tolerance: Plants of the new *Verbena* have been observed to tolerate temperatures from about 5° C. to about 35° C.

Pathogen/pest resistance: Plants of the new *Verbena* have been observed to be resistant to Powdery Mildew. Plants of the new *Verbena* have not been observed to be resistant to pests and other pathogens common to *Verbenas*.

It is claimed:

1. A new and distinct *Verbena* plant named 'Duempstraw' as illustrated and described.

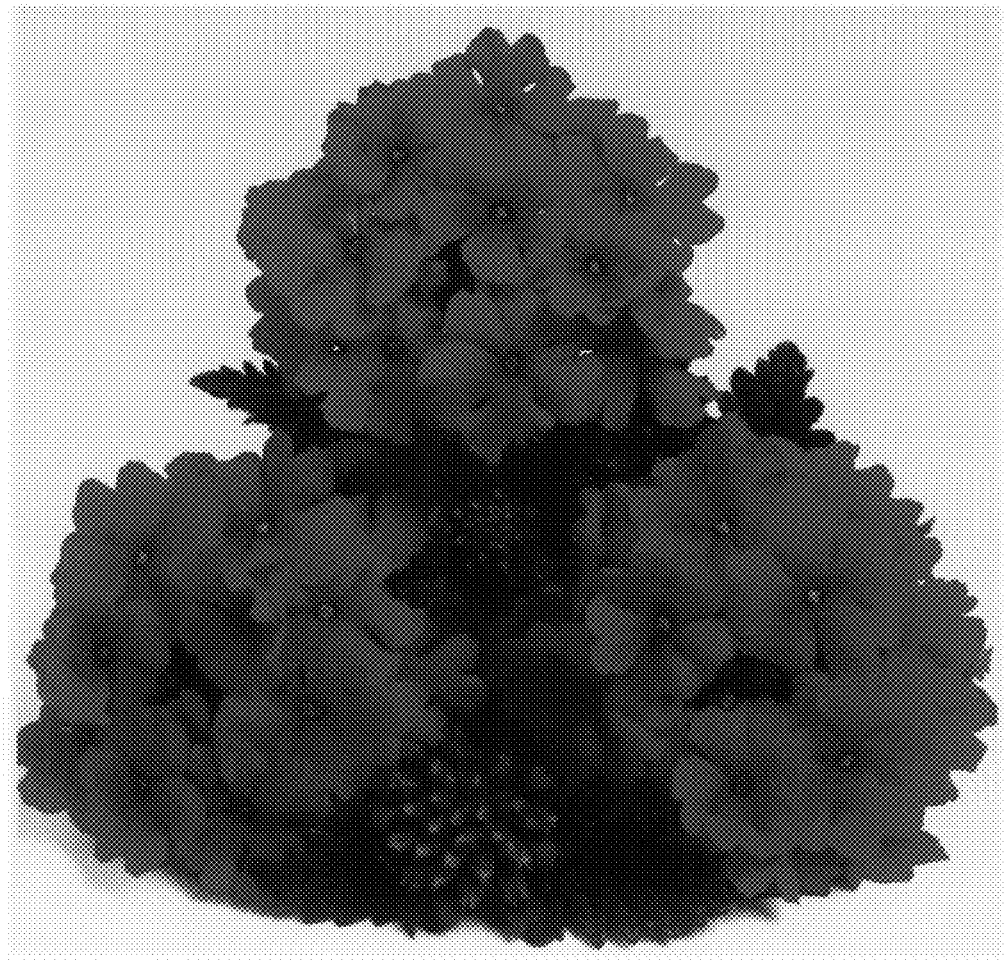

* * * * *